US006268185B1

(12) United States Patent
Page et al.

(10) Patent No.: US 6,268,185 B1
(45) Date of Patent: Jul. 31, 2001

(54) PRODUCTION OF AMINO ACIDS AND ENZYMES USED THEREFOR

(75) Inventors: Michael Ivan Page, Huddersfield (GB); Timothy Mark Beard, Durban (ZA)

(73) Assignee: CIBA Specialty Chemicals Water Treatments Limited, Bradford (GB)

( * ) Notice: Subject to any disclaimer, the term of this patent is extended or adjusted under 35 U.S.C. 154(b) by 0 days.

(21) Appl. No.: 09/230,406

(22) PCT Filed: Jul. 25, 1997

(86) PCT No.: PCT/GB97/02031

§ 371 Date: May 26, 1999

§ 102(e) Date: May 26, 1999

(87) PCT Pub. No.: WO98/04733

PCT Pub. Date: Feb. 5, 1998

(30) Foreign Application Priority Data

Jul. 29, 1996 (GB) .................................. 9615852

(51) Int. Cl.$^7$ ..................................... C12P 13/04
(52) U.S. Cl. ................. 435/106; 435/252.1; 435/280; 435/822
(58) Field of Search ...................... 435/106, 280, 435/252.1, 822

(56) References Cited

U.S. PATENT DOCUMENTS

| 3,971,700 | 7/1976 | Boesten ..................... 195/2 |
| 4,366,250 | * 12/1982 | Jallageas et al. ................ 435/280 |
| 5,034,329 | 7/1991 | Cerbelaud et al. ................ 435/280 |
| 5,215,897 | 6/1993 | Sakashita et al. ................ 435/106 |

FOREIGN PATENT DOCUMENTS

| 0326482 | 8/1989 | (EP) . |
| 0494716 | 7/1992 | (EP) . |
| 2274582 | 1/1976 | (FR) . |
| 2586702 | 3/1987 | (FR) . |
| 92/01062 | 1/1992 | (WO) . |

* cited by examiner

Primary Examiner—Herbert J. Lilling
(74) Attorney, Agent, or Firm—David R. Crichton

(57) ABSTRACT

A process for producing α-amino acid from starting material comprising α-amino amide enantiomers (A) and (B) is such that enantiomer (A) is converted preferentially over enantiomer (B) so that a time independent excess of at least 90%, preferably at least 98% is given. The reaction is catalyzed by an amidase which may in particular be produced by specific Rhodococcus species.

16 Claims, No Drawings

PRODUCTION OF AMINO ACIDS AND ENZYMES USED THEREFOR

This application is a 371 of PCT/GB97/02031 Jul. 25, 1997.

The invention relates to new processes of enantioselective conversion of α-amino amides, α-methyl amides and α-aminomethyl amides to their corresponding acids and to new microorganisms and enzymes useful in these processes.

It is known that α-amino amides may be converted to α-amino acids by hydrolysis. This hydrolysis may be catalyzed by an amidase enzyme. It is also known to convert α-amino nitriles to α-amino acids by first converting the nitrile to an amide by its hydration. This nitrile-to-amide hydration may be carried out using a nitrile hydratase enzyme catalyst.

It is known that these transformations may be carried is out in an enantioselective fashion (that is, the α-amino acid produced has an excess of one enantiomer) by choice of suitable enzymes. For instance, Bauer et al in Appl. Microbiol. Biotechnol. (1994) 42:1–7 describes the conversion of α-amino phenyl acetonitrile to α-amino phenyl acetic acid. The conversion is catalyzed by a strain of *Agrobacterium tumefaciens*. The nitrile is converted in almost stoichiometric amounts to the amide. The amide is then slowly hydrolyzed to the acid. The S enantiomer is preferentially formed. The best enantiomeric excess (97%) appears to be achieved after 43% conversion of the amide.

It appears that it is necessary to terminate the reaction at this point in order to achieve the high enantiomeric excess, ie the conversion does not give time-independent enantioselectivity.

This requirement to stop the reaction at a particular point in order to achieve the best enantiomeric excess is well known in enantioselective hydrolysis of amides to acids. In general, known catalysts of the above mentioned amides to their corresponding acids hydrolyse one amide enantiomer more rapidly than the other and eventually tend to convert a significant amount of the less preferred enantiomer.

Other conversion reactions have been described which appear to give high conversion and enantioselectivity, but do not appear to exhibit tame independent enantioselectivity. For instance, EP-A-332,379 discloses production of various amino acids. These are produced from a nitrile by exposure to various microorganisms. It is not stated whether the effective enzyme catalyst is a nitrilase or a combination of nitrile hydratase and amidase. It is stated that it is essential to carry out the reaction either at a pH between 8 and 12 or in the presence of an aldehyde. U.S. Pat. No. 4,080,259 describes amidase enzymes which effect hydrolysis of various amides to produce amino acids. Where the pH of the reaction mixture is given it appears to be from around 8 to around 10. U.S. Pat. No. 4,366,250 and FR-A-2,626,287 describe enzymic hydrolysis of various natural amino acids. U.S. Pat. No. 3,971,700 describes selective hydrolysis of phenyl glycine amide to give phenyl glycine. None of these references alleges that the reaction described gives time independent enantioselectivity.

U.S. Pat. No. 5,248,608 describes an enantioselective hydrolysis of various α-substituted carboxylic acid amides. The hydrolysis is carried out using an amidase enzyme produced by *Ochrobactrum anthropi* or a Klebsiella sp. The citation alleges that very high conversion and enantiomeric excess are obtained. It explains that the general theory regarding enantioselective conversions described in past publications applies to the process described in U.S. Pat. No. 5,248,608. The publications referred to are those which rely upon stopping the reaction at a particular time in order to obtain a high enantiomeric excess i.e. reactions which do not give time independent enantioselectivity.

This document describes various examples. Some examples are of hydrolysis of α-amino amides but the majority are of other α-substituted amides. Only one of the examples demonstrates time independent enantioselectivity. This single example demonstrates hydrolysis of an N-hydroxy substituted α-amino amide.

Some examples demonstrate hydrolysis of α-amino amides, but none of these show time independent enantioselectivity. Further, the maximum time for reaction which is demonstrated in these examples is 8 hours. The reactions are all carried out as batch reactions.

U.S. Pat. No. 5,215,897 also describes an enantioselective hydrolysis of amino acid amide, which produces mainly L-amino acid. Again the only reactions described are batch reactions which are carried out for a maximum of three hours. The yield in the majority of the reactions is below 50% of the starting mixture and there is no demonstration that the reaction is or could be such that it gives time independent enantioselectivity.

It would be desirable to be able to produce α-amino is amides having a high enantiomeric excess. This is particularly desirable for the production of enantiomerically pure unnatural α-amino acids. It would also be desirable to achieve such enantiomeric purity together with high conversion of the relevant amide enantiomer. It would also be desirable to be able to do this in a manner which provides production processes which are conveniently adaptable to an industrial scale.

According to a first aspect of the invention we provide a process of converting an α-amino amide to an α-amino acid, comprising conducting a conversion reaction catalyzed by an amidase enzyme, in which the α-amino amide starting material comprises amide enantiomers (A) and (B) and in the conversion reaction enantiomer (A) is converted preferentially over enantiomer (B), Characterized in that the amidase enzyme is capable of converting enantiomer (A) such that it gives an enantiomeric excess of at least 90% independently of the conversion time.

In this specification, when we say that the enantiomeric excess is given independently of conversion time, we mean chat the high enantiomeric excess is retained throughout the time there is sufficient of enantiomer (A) to dominate the reaction, that is until most of enantiomer (A) is converted. For instance this can be up to 90% conversion of enantiomer (A). Generally time independent enantiomeric excess is maintained up to 95% and often 100% conversion of enantiomer IA). In some cases time independent enantiomeric excess is remained beyond 100% conversion of enantiomer (A), but this is not essential. The enantiomeric excess is that of the acid product.

Thus in the invention we achieve high selectivity for one enantiomer. In the majority of known processes the enantiomeric excess in the product varies as the conversion reaction progresses and it is often necessary to stop the reaction at a suitable point in order to obtain the best enantiomeric excess. In the invention, however, we achieve high enantiomeric excess at all times during the reaction, ie independently of the conversion time. This is believed to be due to very high selectivity of the amidase for a single enantiomer of the starting material. In known reactions it is usually observed that the amidase converts one enantiomer faster than the other, so that as the reaction progresses the enantiomeric excess tends to decrease. The present process is selective to such an extent that the enantiomeric excess remains at least 90% throughout the reaction.

The starting material in the conversion reaction of the process of the invention is an α-amino amide. The amide is chosen so that it gives on hydrolysis the required α-amino acid.

Suitable α-amino amides used as starting materials have the formula I as follows:

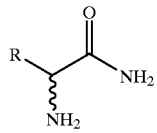

In this preferred formula R is suitably alkyl, cycloalkyl, alkenyl, cycloalkenyl, aryl, alkaryl, aralkyl, $R^1NHCOR^1$, $R^1CONHR^1$, $SO_2R^1$ or $SO_2NHR^1$ in which $R^1$ is alkyl, cycloalkyl, alkenyl, cycloalkenyl, aryl, alkaryl or aralkyl, or substituted versions of any of these. In particular, R can be $C_4$ to $C_9$, for instance $C_4$ to $C_7$, linear or branched alkyl or alkenyl, cyclic alkyl or alkenyl, phenyl, or substituted phenyl in which the substituent is selected from para-$CH_3$, meta-$CH_3$, ortho-$CH_3$, para-$CF_3$, para-Et, para-$(CH_3)_3C$, para-Cl, para-$CH_3(CH_2)_3O$ and para-OH. These substituents, and others, in the meta and ortho positions can be used.

According to the formula I it is particularly preferred that if R is alkyl or alkenyl it, is $C_4$ to $C_9$, for instance $C_4$ to $C_7$, linear alkyl or alkenyl or, in particular, cyclic alkyl. If R is phenyl it is preferred that it is a substituted phenyl, in particular one in which the substituent is selected frown para-$CH_3$, meta-$CH_3$, para-$CF_3$, ortho-$CH_3$, para-Et, para-$(CH_3)_3C$, para-Cl and para-$CH_3(CH_2)_3O$.

The conversion reaction thus produces an α-amino acid of the formula II, as follows:

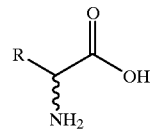

The process of the invention is particularly suitable for the production of unnatural amino acids.

The amide starting material comprises enantiomer (A) and enantiomer (B) Enantiomer (A) is that which it is desired to convert preferentially into the corresponding acid during the conversion reaction. Enantiomer A is usually the L amino acid amide, which gives the L amino acid on conversion.

Enantiomers (A) and (B) can be present in substantially equimolar amounts, that is the starting material is preferably a racemic mixture. However, the process of the invention can also be applied to starting materials which have an enantiomeric excess of greater than zero. The process may be applied to starting materials in which enantiomer (A) is in excess and to those in which enantiomer (B) is in excess.

The process is particularly useful in systems in which the enantiomer (B), which is not desired to be converted preferentially into the corresponding acid, is present in excess. In some types of reaction the ratio of enantiomer (B) to enantiomer (A) will steadily increase during the reaction as the amount of enantiomer (A) is reduced by conversion to the corresponding amino acid. In other types of reaction the supply of enantiomer (A) may be periodically or continuously replenished so that the ratio of enantiomer (A) to enantiomer (B) varies over the course of the reaction both upwards and downwards. Preferably the amount of enantiomer (B) is at least 125% or 150%, preferably at least 200%, more preferably at least 250%, of the amount of enantiomer (A) for at least some of the duration of the reaction, preferably at least 30 minutes, more preferably at least 1 or 2 hours.

The amide starting material may be produced in any suitable manner. It is preferred that the amide is produced by an enzyme catalyzed reaction, especially from nitrile starting material. Therefore in preferred processes of the invention an initial step comprises the conversion of an α-amino nitrile to its corresponding α-amino amide, catalyzed by a nitrile hydratase enzyme. The nitrile hydratase enzyme may be one which preferentially converts one nitrile enantiomer over the other. Generally however the nitrile hydratase acts non-selectively and converts both nitrile enantiomers at substantially the same rate.

The amidase enzyme used in the process of the invention is one which is capable of preferentially converting enantiomer (A) so that it gives an enantiomeric excess of at least 90% independently of the conversion time.

Preferably the time-independent enantiomeric excess is at least 95% more preferably at least 97%, and in particular at least 98%.

The conversion reaction is preferably carried out to such an extent that at least 70% preferably at least 80 or 90%, more preferably at least 95 or 98% and even substantially 100% of enantiomer (A) has been converted to its corresponding acid.

In the conversion reaction of the process of the invention the amidase is chosen so that it converts only very small amounts of enantiomer (B). Preferably at the end of the conversion reaction not more than 10% more preferably not more than 5% or even 2% and often substantially none of enantiomer (B) has been converted to its corresponding acid. In particular, in the process of the invention it is preferred that the amidase is such that it results in less than 10%, preferably less than 5% or even 2%, more preferably substantially no conversion of enantiomer (B) even when the concentration of enantiomer (A) has fallen below detectable levels.

Any conditions suitable for carrying out the amide-to-acid conversion reaction may be used. Conditions are generally chosen to be optimal for the action of the amidase enzyme. The enzyme used in the invention is one which is capable of carrying out the specified conversion. In some circumstances it may be desirable to operate the conversion reaction under conditions which do not give optimal enantiomeric excess. For instance it may be desirable in optimising the economics of the conversion to operate at an elevated temperature. Some enzymes tend to exhibit diminished selectivity to their substrate as temperature increases. Therefore in some cases it may be necessary to strike a balance between selectivity and productivity. However, it is essential in the invention that the amidase enzyme is capable of carrying out the specified conversion under at least some conditions. Preferably the enzyme is capable of carrying out the highly selective conversion at a temperature of from 10 to 50°, often around 30° C. An advantage of the extremely selective enzymes used in the invention is chat they can be operated at higher temperatures than standard amidase enzymes, thus increasing productivity, whilst retaining higher selectivity than standard amidase enzymes.

Temperature in the conversion reaction is usually from 10 to 50° C., preferably 15 to 35° C., often 20 or 30° C.

Any suitable pH may be used for the conversion reaction. Preferably however a pH below 8 is used, in particular 6 to 7.5 or 8 and often around 7. This is in contrast with the process of EP-A-332,379, in which it is essential to use pH of 8 to 12 if an aldehyde is not present. According to the process of the present invention it is possible to carry out the conversion reaction at a pH below 8 in the absence of an aldehyde.

Starting material may be included in the reaction mixture in any desired concentration. Concentrations of 1 mM to 2M are particularly suitable, for instance 5 mM to 1M, often around 10 to 50 mM, in particular up to 20 mM.

The amidase enzyme may be included in the reaction mixture in any suitable form. The amidase enzyme is generally produced by a microorganism. The amidase enzyme may be used in for instance the pure form, having been extracted from a cultured microorganism before use as a catalyst. The extraction method used should ensure that the activity and stability of the amidase are not lost. It may also be used in a semi-pure form, for instance as liquid culture or as a bacterial cell fraction such as intact cells or crushed cells. It may be used in the form of crude, impure enzyme solution. IL may be supported or immobilised on a carrier, such as a cross-linked polymeric matrix, eg cross-linked polyvinyl alcohol or cross-linked polyacrylamide. It may be used in the form of non-swollen particles having surface-bound enzyme. Preferably it is used in the form of intact bacterial cells, free or supported in a cross-linked polymeric matrix.

The duration of the conversion reaction can vary according to the reagents used, conditions chosen and type of reaction. The reaction may be a batch reaction. In a batch reaction all reagents are combined at the beginning of the conversion reaction and allowed co react. In this case it is convenient that the reaction continues for up to for instance four hours, for instance 1 to 3 hours.

Alternatively the reaction may be carried out as a fed batch or continuous reaction. It is one of the advantages of the reaction that due to the time independent enantiomeric excess which is obtained such types of reaction are feasible. These are particularly preferred for use on an industrial scare.

In a fed batch reaction, reactants are placed in a reaction vessel at the beginning of the reaction and allowed to react During the reaction time concentration of starting material will decrease as it is converted to the final product. Therefore during the reaction additional starting material is added. Normally a lower and an upper limit on the concentration of starting material are both set and the starting material is initially supplied so as to have a concentration at the upper level and allowed to fall to the lower level. Additional starting material is then supplied so as to raise its level to the upper limit and so on until the reaction has proceeded to an extent that sufficient product is produced.

In a continuous reaction the reagents are kept in steady state with supply of starting material at the same rate as removal of the reaction mixture from the reaction vessel. In such systems it is particularly desirable to be able to provide a reaction mixture which contains a very low level of starting material and a very high level of reaction product, so that the removed reaction mixture does not need to undergo extensive purification procedures. This is again possible with the process of the invention.

In both fed batch and continuous processes it is a particular advantage of the invention that it may be carried out in the presence of high concentrations of starting material. Preferably during the reaction the ratio of product amino acid to enantiomer A starting material becomes at least 5:4, preferably at least 3:2 and more preferably at least 2:1 or 3:1. Preferably this ratio is maintained in the reaction for at least 30 minutes, more preferably at least 1 or 2 hours.

Fed batch and continuous reactions are also particularly suited to being carried out over extended periods of time, which can be highly desirable on a commercial scale. For instance the conversion reaction may continue for at least eight hours, preferably at least nine hours, and may continue for at least 12 to 15 hours and even up to 24 or 48 hours or more.

It is particularly desirable in the invention that the only enzyme catalyst present in the reaction mixture is an amidase (optionally together with a nitrile hydratase, if this is used to produce the amide starting material). In particular it is preferred that no racemase is present in the conversion reaction mixture. Some conversions are known in which racemase must be used in combination with an amidase which is said to be enantioselective. However these must be carried out in the presence of a racemase enzyme, which we believe continuously converts the enantiomer which is not preferentially converted into a racemic mixture. This is because, we believe, the conversion of amide to acid is not time independent and as the concentration of the unpreferred unreacted enantiomer builds up, conversion of that begins to the corresponding amino acid.

Whatever reaction type is used it is preferred that at the end of the reaction at least 80%, preferably at lest 90 or 95%, more preferably at least 98% and often substantially 100%, of enantiomer A has been converted to its corresponding acid.

Measurement of the enantiomeric excess achieved at the end of the process of the invention can be carried out in any standard manner.

The reaction conditions given for the amide-to-acid conversion reaction are also generally applicable to a nitrile-to-amide conversion reaction if this is included in the process of the invention and when catalyzed using a nitrile hydratase enzyme, with the exception that concentrations of 1 to 100 mM, particularly 5 to 50 or 20 mM, of nitrile are preferred.

At the termination of the process of the invention the enantiomerically pure amino acid will have been produced from enantiomer (A). Large amounts of unconverted enantiomer (B) may also remain in the reaction mixture. In is some cases the enantiomerically pure (B) amide may be required for use and is also a product of the conversion reaction. The converted enantiomer (A) and unconverted enantiomer (B) are generally separated. The enantiomerically pure amino acid derived from enantiomer (A) can then be used as desired. Unconverted enantiomer (B) may also be used as required. If it is desired to obtain the enantiomerically pure amino acid derived from enantiomer (B) then chemical hydrolysis of unconverted enantiomer (B) can be carried out in known manner. If enantiomer (B) is not required, it is particularly efficient to subject it to racemisation and to include the resultant racemic mixture of enantiomers (A) and (B) in a further batch of amide starting material for the process of the invention. Racemisation can be carried out chemically. Alternatively it can be carried out with the use of a racemase enzyme. If enantiomer (B) is subjected to racemisation and the resultant racemic mixture of enantiomers (A) and (B) is then further reacted, conversion of up to loot; of the original starting material can be achieved.

In the process of the first aspect of the invention the amidase enzyme is preferably produced by the microorganism of genus Rhodococcus which has been deposited at the National Collection of Industrial and Marine Bacteria (23 St Machar Drive, Aberdeen, Scotland, UK, AB2 1RY) under accession number NCIMB 40795. This deposit was made under the provisions of the Budapest Treaty on Apr. 19, 1996.

This microorganism is particularly preferred because it produces in addition to an amidase enzyme suitable for use in the process of the invention a nitrile hydratase enzyme. This acts non-enantioselectively. Thus using this single microorganism Rhodococcus NCIMB 40795 enantioselective conversion of α-amino nitrile to α-amino acid via α-amino amide can be conducted.

This microorganism is in itself a new strain of microorganism. Therefore according to a second aspect of the invention we provide a microorganism which is Rhodococcus NCIMB 40795 or a mutant thereof having the ability to produce an amidase. This new microorganism is useful for the conversion of nitriles and amides to α-amino acids. According to a third aspect of the invention we also provide a process of converting an α-amino amide to an α-amino acid comprising conducting a conversion reaction catalyzed by an amidase enzyme, in which process the α-amino amide starting material comprises amide enantiomers (A) and (B) and in the conversion reaction enantiomer (A) is converted preferentially over enantiomer (B), characterized in that the amidase enzyme is produced by Rhodococcus NCIMB 40795. This process preferably has any or all of the features discussed above in connection with the process of the first aspect of the invention.

The Rhodococcus strain of the invention is believed to be an atypical strain of this genus. It is Gram-Positive, gives no spores and is non-motile. It grows well at 30° C. and less well at 37° C. and 41° C. but not at 45° C. It shows catalyze activity but not oxidase activity and is not fermentative in glucose OF.

The cell wall diamino acid is meso DAP. Mycolic acids are present. The fatty acid profile includes the following:

tetradecanoic acid, pentadecanoic acid, hexadecenoic acid, hexadecanoic acid, heptadecenoic acid, heptadecanoic acid, octadecenoic acid but very little tuberculostearic or other 10 methyl branched acids (less than 1% of each).

The invention also provides new enantioselective amidase enzymes. An amidase enzyme of the fourth aspect of the invention is obtainable by culturing Rhodococcus NCIMB 40795 or a mutant thereof capable of producing an amidase.

We have also found that a second specific microorganism strain is particularly useful in carrying out the process of the invention. This is a strain of the species *Rhodococcus wratslaviensis* deposited at the National Collection of Industrial and Marine Bacteria under accession number NCIMB 13082, named as *Tsukamurella wratslaviensis*. This microorganism produces an amidase which can carry out the process of the invention.

The invention also provides processes in which α-methyl amides and α-aminomethyl amides are converted to their corresponding acids. Thus according to a fifth aspect of the invention we provide a process of converting an α-methyl amide or an α-aminomethyl amide to an α-methyl acid or an α-aminomethyl acid, comprising conducting a conversion reaction catalyzed by an amidase enzyme, in which the α-methyl amide or α-aminomethyl amide starting material comprises amide enantiomers (A) and (B) and in the conversion reaction enantiomer (A) is converted preferentially over enantiomer (B), characterized in that the amidase enzyme is capable of converting enantiomer (A) such that it gives an enantiomeric excess of at least 90% independently of the conversion time.

In this process of the fifth aspect of the invention the α-methyl amide is suitably of the formula III as follows:

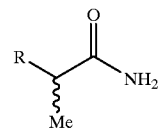

in which R may be any of the groups discussed above for R in formula I.

The α-aminomethyl amide suitably has the formula IV as follows:

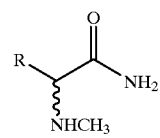

in which R has any of the values suggested for R in formula I above.

The conversion reactions of the α-methyl amide and α-aminomethyl amide produce α-methyl acids and α-aminomethyl acids respectively, of the formulae V and VI, as follows:

(V)

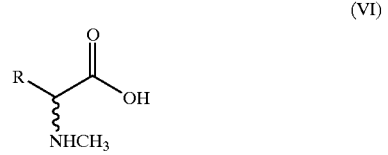

(VI)

Any of the features of the process of the first aspect of the invention may be applied to the process of the fifth aspect of the invention.

We find that the α-methyl amides and α-aminomethyl amides tend to be converted, especially by the amidase from the microorganism Rhodococcus NCIMB 40795, at a slower rate than the α-amino acids.

Products of any of the processes of the invention are highly enantiomerically pure. They are particularly useful as intermediates in the preparation of pharmaceuticals and agrochemicals, for instance antibiotics.

The following are some examples of the invention.

EXAMPLE 1

Culture of Microorganism

The original isolate Rhodococcus NCIMB 40795 was cultured using 500 ml shake flasks, with orbital shaking (200 rpm) at 30° C.

The culture medium was prepared as shown below, with all quantities in g/l unless otherwise stated:

| | |
|---|---|
| Dipotassium hydrogen phosphate | 7.0 |
| Potassium dihydrogen phosphate | 3.0 |
| Sodium acetate | 5.0 |
| Propionitrile | 714 µl |
| Magnesium sulphate* | 1.0 |
| Calcium chloride* | 0.2 |
| [*autoclaved separately] | |
| Vitamins (at 1 ml/l) | g/l |
| Thiamine hydrochloride | 0.1 |
| Calcium pantothenate | 0.1 |
| Pyridoxine hydrochloride | 0.1 |
| Biotin | 0.01 |
| Inositol | 10.0 |
| Trace metals (at 5 ml/l) | g/l |
| MgO | 10.75 |
| $CaCO_3$ | 2.0 |
| $FeSO_4 \cdot 7H_2O$ | 4.5 |
| $ZnSO_4 \cdot 7H_2O$ | 1.44 |
| $MnSO_4 \cdot 4H_2O$ | 1.12 |
| $CuSO_4 \cdot 5H_2O$ | 0.25 |
| $CaSO_4 \cdot 7H_2O$ | 0.28 |
| $H_3BO_3$ | 0.06 |
| HCl (6 N) | 51.3 cm$^3$ |

The cells were harvested in late exponential growth by centrifugation at 10,000 rpm for 20 minutes. The cell pellet was washed with saline (250 ml) and centrifuged again under the same conditions.

The cell pellet was then frozen until needed for use in the conversion reaction.

EXAMPLE 2

Conversion of α-Amino Nitrile

Phenylglycinonitrile (16.8 mg, 0.1 mmol) was dissolved in phosphate buffer (10 ml, pH 7.0, 50 mM) to give a 10 mM concentration. The solution was incubated with whole cells produced as described in Example 1 (at 4.2 g/L [dry cells] at 20° C. and samples taken as outlined below:

A 50 µl sample was removed and diluted with 450 µl water. The cells were removed by microcentrifugation (13,000 rpm, 30 seconds). The supernatant was decanted off, and HCl (10 µl, 6N) was added The mixture was extracted with dichloromethane to removed any aldehyde formed by the degradation of the nitrile, which would interfere with the HPLC. The aqueous phase was then analysed by HPLC.

All HPLC was run using a LDC/Milton Ray ConstaMetric 3 with a UV detector.

| | |
|---|---|
| Column | Phenomenex RP select B (25 cm × 0.46 cm) |
| Flow rate | 1 ml min$^{-1}$ |
| Wavelength | 254 nm |
| Eluent | 95% Tris/HCl buffer (10 mM, pH 3): 5% methanol |
| Retention | Acid 6.7 minutes, Amide 8.0 minutes, Nitrile 13.6 minutes |

After 10% conversion, a sample (200 µl) was taken and extracted with dichloromethane to remove any unreacted nitrile. This was refluxed in HCl (6N) until HPLC showed that all the amide had been converted to acid. The acid was then subjected to chiral HPLC as outlined below:

| | |
|---|---|
| Column | Sumichiral OA 5000 (15 cm × 0.46 cm) |
| Flow rate | 1 ml min$^{-1}$ |
| Wavelength | 254 nm |
| Eluent | 90% $CuSO_4$ (3 mM): 10% methanol |
| Retention | Enantiomer 1:- 18 minutes, Enantiomer 2:- 30 minutes |

The amide produced was found to be racemic, i.e. the nitrile hydratase is not enantioselective.

In this case the reaction was inhibited by cyanide produced by the degradation of the nitrile. However it was possible to achieve 100% conversion of the nitrile by adding more cells.

EXAMPLE 3

Conversion of α-Amino Amide

4 Chloro phenyl α-amino acetamide (11 mg, 0.05 mmol) was dissolved in phosphate buffer (5 ml, pH 7.0, 50 mM) to give a 10 mM concentration. The solution was incubated at 30° C. and the whole cells produced as described in Example 1 were added (at 4.2 g(dry cells) /1). Samples were taken at various time intervals as outlined below:

Sample at time=0 mins:

1. A 50 µl sample was removed and diluted with 450 µl water. The cells were removed by microcentrifugation (13,000 rpm, 30 seconds) and the sample analysed by HPLC.

| | |
|---|---|
| Column | Phenomenex RP select B (25 cm × 0.46 cm |
| Flow rate | 1 ml min |
| Wavelength | 254 nm |
| Eluent | 80% Tris/HCl buffer (10 mM, pH 3): 20% methanol |
| Retention | Acid 6.7 minutes, Amide 8.0 minutes |

2. A 200 µl sample was removed and centrifuged as above. This was subjected to chiral HPLC as outlined below:

| | |
|---|---|
| Column | Sumichiral OA 5000 (15 cm × 0.46 cm) |
| Flow rate | 1 ml min$^{-1}$ |
| Wavelength | 254 nm |
| Eluent | 75% $CuSO_4$ (3 mM): 25% methanol |
| Retention | Enantiomer 1: – 25 minutes, Enantiomer 2: – 40 minutes. |

Samples were analysed subsequently at various times by method 1 until it was observed that 50% conversion of the amide had been achieved. At this point sampling methods 1 and 2 were again used.

It was observed that the concentration of amide decreased from 10 mM to around 5.0 mM over a period of around 140 minutes. Over the same period the concentration of 4-chlorophenyl α-amino acetic acid increased from 0 to around 5.0 mM. After around 145 minutes it could be seen that the natural termination of the reaction had occurred as the rate was then substantially zero.

The same procedure was adopted with other substituted and unsubstituted phenyl α-amino acetamides and with cyclic and acyclic aliphatic amides. Results are shown in Table 1 below.

General Formula I

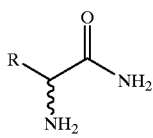

| R | % Conversion | % e.e. |
|---|---|---|
| para-H-phenyl | 50 | >98 |
| para-CH₃-phenyl | 50 | >98 |
| meta-CH₃-phenyl | 50 | >98 |
| ortho-CH₃-phenyl | 50 | >98 |
| para-CF₃-phenyl | 50 | >98 |
| para-Et-phenyl | 50 | >98 |
| para-(CH₃)₃C-phenyl | 50 | >98 |
| para-Cl-phenyl | 5o | >98 |
| para-CH₃(CH₂)₃O-phenyl | 50 | NOT DETERMINED |
| para-OH-phenyl | 50 | >98 |
| $C_4H_9$ | 50 | >98 |
| $C_9H_{15}$ | 50 | >98 |
| cyclohexyl | 50 | >98 |
| methylcyclohexyl | 50 | >98 |
| (CH₃)₂CHCH₂ | 50 | >98 |
| para-CH₃O-phenyl | 50 | >98 |
| phenyl-CH₂— | 50 | >98 |

EXAMPLE 4

α-phenyl α-amino acetamide (75 mg, 0.5 mmol) was dissolved in phosphate buffer (5 ml, pH 7.0, 50 mM) to give a 10 mM concentration. The solution was incubated at 30° C. and the whole cells produced as described in Example 1 were added (at 4.2 g (dry cells)/L) Samples were taken at various time intervals as outlined below.

Sample at time=0 mins

1. A 45 μl sample was removed and diluted with 450 μl water. The cells were removed by microcentrifugation (13,000 rpm, 30 seconds) and the sample analysed by HLPC.

| Column: | Phenomenex RP Select B (25 cm x 046 cm) |
|---|---|
| Flow Rate: | 1 ml min⁻¹ |
| Wavelength: | 254 nm |
| Eluent: | 95% Tris/HCl buffer (10 mM, pH 3): 5% methanol |
| Retention: | Acid 4.7 minutes, Amide 5.8 minutes |

2. A 200 μl sample was removed, centrifuged as above. This was subjected to chiral HPLC as outlined below.

| Column: | Sumiiral OA 5000 (15 cm x 0.4 cm) |
|---|---|
| Flow Rate: | 1 ml min⁻¹ |
| Wavelength: | 254 nm |
| Eluent: | 90% CuSO4 (2 mM): 10% methanol |
| Retention: | L Enantiomer of α-phenyl α-amino acetic acid - 18 minutes |
| | D Enantiomer of α-phenyl α-amino acetic acid - 30 minutes |

Samples were analysed subsequently at various times by method 1 until it was observed that 50% conversion of the amide had been achieved. At this point sampling methods 1 and 2 were used.

It was observed that the concentration of amide decreased from 10 mM to around 5.0 mM over a period of 24 hours. Over the same period the concentration of α-phenyl α-amino acetic acid increased from 0 to around 5 mM. After 48 hours the concentrations of both the amide and the α-phenyl α-amino acetic acid were still at around 5 mM. Therefore, at around 24 hours incubation time it could be seen that the natural termination of the reaction had occurred.

EXAMPLE 5

Whole cells produced as described in Example 1 were added (at 4.2 g (dry cells)/L) to 32 ml of 50 mM, pH 7 sodium phosphate buffer at 35° C. α-phenyl α-amino acetamide solution (8 ml of 50 mM) was added to the cell suspension to give a concentration of 10 mm α-phenyl α-amino acetamide. Samples were taken at various time intervals as outlined below:

Sample time=0 minutes

1. A 0.5 ml sample was removed and the cells removed by microcentrifugation (13,000 rpm, 30 seconds). The supernatant was diluted by a factor of 5 and analysed by HPLC using the conditions described in Example 4.

2. A 200 μl sample was removed, centrifuged as above. The supernatant was subjected to chiral HPLC as outlined in Example 3. Samples were analysed subsequently at 20 minute intervals by method 1. After 4 hours it was observed that 30% conversion of the amide had been achieved. At this point sampling methods 1 and 2 were used.

It was observed after 4 hours that the concentration of amide had decreased from 10 mM to around 7 mM and that the concentration of α-phenyl α-amino acetic acid had increased from o to 3 mM. When the supernatant was analysed by method 2 it was seen that upon 30% conversion of the amide substantially a >98% enantiomeric excess of the L enantiomer of α-phenyl α-amino acetic acid was achieved.

A further 6 ml of 50 mM α-phenyl α-amino acetamide was then added to the cell suspension so that the cell suspension then contained whole cells at 3.57 g(dry cells)/L, 2.55 mM of the enantiomer of α-phenyl α-amino acetic acid and 13.45 mM of amide.

It was observed that the concentration of amide had decreased from 13.45 mM to 10 mM and that the concentration of α-phenyl α-amino acetic acid had increased from 2.55 to 6 mM. When the supernatant was analysed by method 2 it was seen that substantially a >98% enantiomeric excess of the L enantiomer of α-phenyl α-amino acetic acid was achieved.

EXAMPLE 6

Whole cells produced as described in Example 1 were combined with 10 mM α-phenyl α-amino acetamide under conditions as described in Example 5. Samples were taken at various time intervals and analysed as described in Example 5.

It was observed that after 90 minutes the concentration of α-phenyl α-amino acetic acid had increased from 0 to 3.24 mM. At this point sufficient quantity of α-phenyl α-amino acetamide was added to raise its concentration in the reaction mixture by 10 mM. It was observed that after a further 90 minutes, the concentration of α-phenyl α-amino acetic acid had increased to 5.86 mM. At this point sufficient quantity of α-phenyl α-amino acetamide was added to raise its concentration in the reaction mixture by 10 mM. Upon analysis by method 1. It was observed that after a further 90 minutes, the concentration of α-phenyl α-amino acetic acid had increased to 7.98 mM. The cells were then separated from the reaction mixture by centrifugation at 13000 g for 10 minutes. When the supernatant was analysed by method 2 it was seen that substantially a >98% enantiomeric excess of the L enantiomer of α-phenyl α-amino acetic acid was achieved.

EXAMPLE 7

To the 17.26 g of final supernatant produced in Example 6, was added 20.74 g of water to reduce L-α-phenyl α-amino acetic acid concentration to 3.70 mM. To this solution 0.65 g of whole cells produced as described in Example 1 was added.

It was observed that after 45 minutes the concentration of α-phenyl α-amino acetic acid had risen to 3.75 mM. At this point a sufficient quantity of α-phenyl α-amino acetamide was added to the reaction mixture to raise its concentration in the reaction mixture by 12 mM. It was observed that after a further 120 minutes the concentration of α-phenyl α-amino acetic acid had increased to 7.98 mM. The procedure of adding further α-phenyl α-amino acetamide followed by 2 hours incubation as described above was repeated twice again. Upon analysis by method 1, it was observed that the concentration of α-phenyl α-amino acetic acid had increased to 14.81 mM. The cells were then separated from the reaction mixture and analysed by method 2 as described in Example 6. It was seen that substantially a >98% enantiomeric excess of the L enantiomer of α-phenyl α-amino acetic acid was achieved.

EXAMPLE 8

Whole cells produced as described in Example 1 (0.52 g) were added to the final supernatant produced in Example 7.

It was observed that after 40 minutes of incubation at 35° C. the concentration of α-phenyl α-amino acetic acid had increased to 17.46 mM.

On three separate occasions sufficient quantity of α-phenyl α-amino acetamide was added to the reaction mixture to raise its concentration by 12 mM. After each addition the reaction mixture was allowed to incubate for 120 minutes. Upon analysis by method 1 of the reaction mixture and after the completion of the procedure described above, it was observed that the concentration of α-phenyl α-amino acetic acid had increased to 26.64 mM. The cells were then separated from the reaction mixture and analysed by method 2 as described in Example 6. It was seen that substantially a >98% enantiomeric excess of the L enantiomer of α-phenyl α-amino acetic acid was achieved.

EXAMPLE 9

Whole cells produced as described in Example 1 (0.48 g) were suspended in the final supernatant produced in Example 8.

On two separate occasions sufficient quantity of α-phenyl α-amino acetamide was added to the reaction mixture to raise its concentration by 10 mM. After each addition the reaction mixture was allowed to incubate at 35° C. for 120 minutes. Upon analysis by method 1 of the reaction mixture and after the completion of the procedure above, it was observed that the concentration of α-phenyl α-amino acetic acid had increased to 30.38 mM. The cells were then separated from the reaction mixture and analysed by method 2 as described in Example 6. It was found that substantially a >98% enantiomeric excess of the L enantiomer of α-phenyl α-amino acetic acid was achieved.

EXAMPLE 10

Whole cells produced as described in Example 1 (1.07 g) were suspended in 36.9 ml of the L enantiomer of α-phenyl α-amino acetic acid (purchased from Aldrich).

Sufficient quantity of α-phenyl α-amino acetamide was then added to give an α-phenyl α-amino acetamide concentration of 50 mM and dilute the L enantiomer of α-phenyl α-amino acetic acid to 40 mM. The reaction mixture was then allowed to incubate at 30° C. for 300 minutes. After 300 minutes it was observed that an approximately 30% conversion of the amide had been achieved. At this point sampling methods 1 and 2 were used.

It was observed after 300 minutes that the concentration of α-phenyl α-amino acetic acid had increased from 40 mM to 52.6 mM. When the supernatant was analysed by method 2, it was seen that upon an approximately 30% conversion of the amide, substantially a >98% enantiomeric excess of the L enantiomer of α-phenyl α-amino acetic acid was observed.

After a further 960 minutes incubation at 35° C., it was observed that a 40% conversion of the amide had been achieved. At this point sampling methods 1 and 2 were used.

It was observed after 960 minutes that the concentration of α-phenyl α-amino acetic acid had increased to 58.3 mM. When the supernatant was analysed by method 2, it was seen that upon an approximately 40% conversion of the amide, substantially a >98% enantiomeric excess of the L enantiomer of α-phenyl α-amino acetic acid was observed.

These results show the excellent enantiomeric excess which can be achieved using the invention. In particular it will be seen that 50% conversion of the starting material, ie substantially 100% of enantiomer (A), is achieved. This result is also achieved over a wide range of α-amino amides. Such results can be achieved also in the presence of large excesses of the unconverted enantiomer B (in this case the D enantiomer) and in the presence of high concentrations of the product acid.

What is claimed is:

1. A process of converting an α-amino amide to an α-amino acid comprising conducting a conversion reaction catalyzed by an amidase enzyme, in which the α-amino amide starting material comprises amide enantiomers (A) and (B) and in the conversion reaction enantiomer (A) is converted preferentially over enantiomer (B), characterized in that the amidase enzyme is produced by Rhodococcus NCIMB 40795 or *Rhodococcus wratslaviensis* NCIMB 13082, and in which the amidase enzyme is capable of converting enantiomer (A) such that it gives an enantiomeric excess of at least 90% independently of the conversion time.

2. A process according to claim 1 in which the amidase enzyme is capable of converting enantiomer (A) such that it gives an enantiomeric excess of at least 98% independently of the conversion time.

3. A process according to claim 1 in which the α-amino amide starting material is a racemic mixture of enantiomers (A) and (B).

4. A process according to claim 1 in which the enantiomer (B) is present in excess over enantiomer (A) for at least 30 minutes during the conversion reaction.

5. A process according to claim 4 in which the amount of enantiomer (B) is at least 150% of the amount of enantiomer (A) for at least 30 minutes during the conversion reaction.

6. A process according to claim 1 in which the α-amino amide has the formula I:

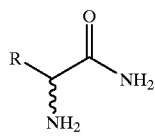

in which R is alkyl, cycloalkyl, alkenyl, cycloalkenyl, aryl, alkaryl; aralkyl, $R^1NHCOR^1$, $R^1CONHR^1$, $SO_2R^1$ or $SO_2NHR^1$ in which $R^1$ is alkyl, cycloalkyl, alkenyl, cycloalkenyl, aryl, alkaryl or aralkyl, or substituted versions of any of these, preferably $C_4$ to $C_9$ linear or branched alkyl or alkenyl, cyclic alkyl or alkenyl, phenyl, or substituted phenyl in which the substituent is selected from para-$CH_3$, meta-$CH_3$, ortho-$CH_3$, para-$CF_3$, para-Et, para-$(CH_3)_3C$, para-Cl, para-$CH_3(CH_2)_3O$ and para-OH.

7. A process according to claim 1 in which the α-amino acid is an unnatural amino acid.

8. A process according to claim 1 in which the enantiomer (A) is the L-enantiomer and is converted into the L α-amino acid.

9. A process according to claim 1 in which an enantiomeric excess of at least 98% is given independently of the conversion time.

10. A process according to claim 1 which is a fed batch process.

11. A process according to claim 1 in which the conversion reaction has a duration of at least 12 hours.

12. A process according to claim 1 in which the α-amino acid corresponding to enantiomer (A) is present in the reaction mixture in excess over enantiomer (A) for at least 30 minutes during the conversion reaction.

13. A process according to claim 4 in which the ratio of α-amino acid corresponding to enantiomer (A) to enantiomer (A) itself is at least 3:2.

14. A process of converting an α-amino amide to an α-amino acid comprising conducting a conversion reaction in which the α-amino amide starting material comprises amide enantiomers (A) and (B) and in the conversion reaction enantiomer (A) is converted preferentially over enantiomer (B), characterized in that the conversion is brought about by contacting the starting material with cell material from Rhodococcus NCIMB 40795 or *Rhodococcus wratslaviensis* NCIMB 13082.

15. A process of converting an α-methyl amide or an α-aminomethyl amide to an α-methyl acid or an α-aminomethyl acid, comprising conducting a conversion reaction catalyzed by an amidase enzyme, in which the α-methylamide or α-aminomethyl amide starting material comprises amide enantiomers (A) and (B) and in the conversion reaction enantiomer (A) is converted preferentially over enantiomer (B), characterized in that the amidase enzyme is produced by Rhodococcus NCIMB 40795 or *Rhodococcus wratslaviensis* NCIMB 13082.

16. A process of converting an α-methyl amide or an α-aminomethyl amide to an α-methyl acid or an α-aminomethyl acid, comprising conducting a conversion reaction catalyzed by an amidase enzyme, in which the α-methylamide or α-aminomethyl amide starting material comprises amide enantiomers (A) and (B) and in the conversion reaction enantiomer (A) is converted preferentially over enantiomer characterized in that the amidase enzyme is capable of converting enantiomer (A) such that it gives an enantiomeric excess of at least 90% independently of the conversion time characterized in that the conversion is brought about by contacting the starting material with cell material from Rhodococcus NCIMB 40795 or *Rhodococcus wratslaviensis* NCIMB 13082.

* * * * *